United States Patent [19]

Sun

[11] 4,093,672
[45] June 6, 1978

[54] PROCESS FOR THE RECOVERY OF ULTRAHIGH PURITY INDENE

[75] Inventor: Yun Chung Sun, Midland, Mich.

[73] Assignee: The Dow Chemical Company, Midland, Mich.

[21] Appl. No.: 815,965

[22] Filed: Jul. 15, 1977

Related U.S. Application Data

[63] Continuation-in-part of Ser. No. 691,129, May 28, 1976, abandoned.

[51] Int. Cl.² ............................................... C07C 7/14
[52] U.S. Cl. ........................... 260/674 R; 260/674 A; 62/532
[58] Field of Search .......... 260/674 R, 674 A, 674 N; 62/532

[56] References Cited

U.S. PATENT DOCUMENTS 3,804,915   4/1974   Schmid et al. ................... 260/674 A Primary Examiner—C. Davis
Attorney, Agent, or Firm—R. S. Carter; G. R. Plotecher

[57] ABSTRACT

Indene is recovered in ultrahigh purity from a liquid hydrocarbon mixture comprising indene and organic impurities of which at least one has a melt point above indene and of which at least one has a melt point below indene by a process comprising (1) crystallizing a substantial portion of indene from the mixture and (2) separating the mother liquor from the crystalline indene by passing a non-reactive gas through the crystalline indene.

6 Claims, No Drawings

4,093,672

PROCESS FOR THE RECOVERY OF ULTRAHIGH PURITY INDENE

CROSS-REFERENCE TO RELATED APPLICATION

This application is a continuation-in-part of application Ser. No. 691,129, filed May 28, 1976, and now abandoned.

BACKGROUND OF THE INVENTION

This invention relates to a process for the recovery of indene in high purity from mixtures of indene and organic impurities.

The art contains many examples of processes for the separation of an organic compound, such as indene, from mixtures with other organic compounds. Because of the presence of other species with close boiling points in indene rich naphtha cracker streams, the highest purity economically attainable by fractional distillation is only about 85 to 92 percent by weight. A process is disclosed in U.S. Pat. No. 1,943,078 to Kahl for the recovery of indene from fractional distillation to obtain a mixture of at least about 80 percent indene. The temperature of this mixture is then lowered to about −25° C to crystallize the indene present. Centrifugation produced a compound having the freezing point of indene (−2° C) in about 47 percent yield. Typically indene purities as high as about 98 weight percent can be obtained by the skillful crystallization and centrifugation of mixtures of this type. Centrifugation is, however, a high energy, high maintenance unit operation and it would be desirable to provide a method which avoids these costs.

Schmid et al., USP AT. No. 3,804,915, teach a process for recovering p-xylene at purities greater than 99.5 weight percent from mixtures of o—, m—and p-xylene. The process comprises crystallizing p-xylene from the xylene mixture at a low temperature, removing the crystals from the mother liquor, and subsequently passing an inert medium through the crystals to remove any adhering mother liquor. However, all the components of the mother liquor have melt points below that of p-xylene.

SUMMARY OF THE INVENTION

According to this invention, indene is recovered in ultrahigh purity from liquid hydrocarbon mixtures, the mixtures comprising indene and organic impurities of which at least one has a melt point above indene and of which at least one has a melt point below indene, the mixture having a co-crystallization temperature at least about 5° C lower than the freezing temperature of the mixture, the process comprising:

(a) crystallizing a substantial portion of the indene from the mixture to form a slurry composed of mother liquor and crystals of indene; and (b) separating the impurities from the resulting crystals by passing a non-reactive gas at a temperature in the range between the freezing and the co-crystallization temperatures of the mixture over the surface of the crystals to remove said impurities while maintaining the crystals and the residual mother liquor at a temperature in the range between the freezing and the co-crystallization temperature of the mixture. The freezing temperature of the mixture is that temperature at which crystallization of the compound commences. Such temperature is always below the freezing point of the compound to be recovered. The co-crystallization temperature of the mixture is defined as the temperature at which the second component of at least a two-component mixture begins to crystallize from the mixture. A substantial portion of the compound is at least about 60 weight percent of the compound.

Surprisingly, the practice of the process of this invention can yield indene in an ultrahigh purity of greater than 98 weight percent. Such purity is not readily achieved by more conventional processes involving expensive centrifugation and/or distillation steps. Moreover, indene is recovered from mixtures comprising organic impurities some of which have melt points below indene, such as diethyl benzene, isopropyl toluene, etc., and some of which have melt points above indene, such as biphenyl, naphthalene, etc.

Ultrahigh purity indene is useful, for example, as a monomer to improve the surface properties of polymers with minimal loss to vaporization due to its high vapor pressure.

DETAILED DESCRIPTION OF THE INVENTION

This invention is suitably practiced in the recovery of indene from a liquid hydrocarbon mixture comprising as little as 50 weight percent of the compound to be recovered. Recovery is suitably accomplished from such a mixture only if the organic impurities crystallize at a temperature at least 5° C below the crystallization temperature of indene. Most advantageously the present invention is practiced in the recovery of indene in ultrahigh purity from a mixture containing at least about 85 weight percent indene and a remaining amount of hydrocarbon impurities all of which crystallize at a temperature at least 15° C below the freezing point of indene. Such mixtures are readily obtained from any suitable hydrocarbon source, such as naphtha cracking or coal oil fractionation. For the purposes of this invention, the term "ultrahigh purity" means a purity of at least 95 weight percent, preferably greater than 98 weight percent, and most preferably greater than 99 weight percent.

The process of the present invention involves the critical operations of (1) crystallizing indene from a liquid mixture of compounds to form a solid-liquid mixture (a slurry) of crystalline indene and liquid impurities (mother liquor) and (2) separating the crystalline indene from the mother liquor by flushing the crystalline indene with a non-reactive gas such that the residual mother liquor is removed. As used herein, a non-reactive gas is one that does not combine chemically with either indene or any of the impurities present in the mixture under the conditions of the process. The non-reactive gas performs a dual function in that it both flushes and vaporizes the mother liquor from the crystals. The residual mother liquor is that mother liquor which is not removed by simple mechanical separation such as decantation.

Of the several alternative procedures for practicing the aforementioned process, it is most advantageously practiced by crystallizing indene from a mixture containing at least 85 weight percent indene and then collecting the crystalline indene in a manner such that the non-reactive gas is passed through the crystalline solid as the solid is being collected.

As an example of this procedure, the mixture is placed in an airtight vessel and agitated while being cooled to the freezing temperature of the mixture. Once a substantial portion of indene has been crystallized, the mother liquor containing the liquid impurities is separated from the slurry while maintaining the crystals and the residual mother liquor at a temperature between the freezing temperature and the co-crystallization temperature of the mixture. Separation of the mother liquor in this manner is most beneficially achieved by passing a non-reactive gas through the crystallized indene such that intimate contact of the indene particle surfaces and the non-reactive gas is achieved thereby flushing and vaporizing the mother liquor from the crystalline indene.

Alternatively, a procedure may be employed wherein other separation steps are used in addition to the aforementioned critical operations. While such a lengthy procedure can be practiced using the more concentrated mixtures, it is particularly effective for the recovery of indene from mixtures containing less than about 85 weight percent. As an example, crystallization of indene is effected by cooling the mixture to a temperature below the freezing temperature of the mixture. A portion of the mother liquor is mechanically separated from the slurry containing the crystals in a conventional manner, e.g., decantation, filtration and/or centrifugation. This separation stage makes more efficient the separation caused by the flushing of the non-reactive gas. The remainder of the mother liquor is removed and the compound is recovered by passing a non-reactive gas over the surfaces of the crystals and the residual mother liquor to remove the residual mother liquor from the crystals while maintaining the crystals and residual mother liquor at a temperature in the range between the freezing and co-crystallization temperatures of the mixture.

Other processes which comprise the critical operations of crystallization of indene from a liquid mixture with organic impurities and removal of at least a residual portion of the mother liquor from the crystallized indene by passing a non-reactive gas through the crystals are also suitable embodiments of the present invention.

Crystallization of indene present in the mixture is advantageously accomplished by lowering the temperature of the mixture to a temperature between the freezing temperature and the co-crystallization temperature of the mixture to form a slurry of mother liquor and indene crystals. Preferably the mixture is lowered to a temperature between about 10° C below the freezing temperature of the mixture and about 5° C above the co-crystallization temperature of the mixture. In the recovery of indene from hydrocarbon mixtures, the preferred temperature is between about −10° C and about −20° C. For the process to recover indene in the highest purity, the co-crystallization temperature should be at least about 5° C lower than the freezing temperature of the mixture and preferably at least about 15° C lower than the freezing temperature.

The temperature of the mixture is lowered at a rate and under conditions of agitation such that entrapment of impurities in the crystals is minimized and that crystals are produced which, when subjected to the flow of the non-reactive gas, form a mass of high porosity to assure adequate crystal surface to gas contact. For example, starting with the mixture at a temperature higher than the freezing temperature of indene, the temperature of the mixture is lowered at a rate between about 3° C per hour and about 25° C per hour, and preferably at a rate between about 10° C per hour and about 15° C per hour. The foregoing rate of temperature lowering is typically accompanied with a degree of agitation of the mixture consistent with the aforementioned objectives of minimum entrapment and maximum porosity of the mass of crystals. Generally the crystals are larger than 0.2 mm in one dimension, and preferably larger than 0.2 mm in each of the three dimensions. Most preferably, the crystals are from about 2 to about 5 mm in each of the three dimensions. Crystals about 2 mm in length are readily prepared and occasionally crystals as large as 5 mm in length are prepared. The porosity of the mass of crystals of less than about 0.2 mm in length to the flow of the non-reactive gas is typically poor and the production of crystals smaller than 0.2 mm should be minimized.

To separate the mother liquor from the crystals, the flushing and vaporizing action of a non-reactive gas is used. Non-reactive gases such as nitrogen or carbon dioxide can be used. In the case of an extremely wet slurry, it may be advantageous to carry out an initial separation step before the use of the gas. Such separations can be done by any solid-liquid separation process, such as, for example, filtration and/or centrifugation. The non-reactive gas is passed over the surfaces of the crystals at a rate and in an amount such that removal of the mother liquor from the crystals and vaporization of the residual mother liquor is accomplished by the flow of the non-reactive gas. The pressure differential needed to cause the flow can be supplied by either a supply of the gas at a pressure above atmospheric which is exhausted through the slurry to the atmosphere or a vacuum which pulls the gas through the slurry. The flow is maintained for a period of time sufficient to vaporize essentially all of the residual mother liquor.

The non-reactive gas is passed through the slurry at a rate sufficient to remove essentially all of the residual mother liquor. As used herein, "essentially all" means that the slurry contains less than 5, preferably less than 2, and most preferably less than 1 weight percent mother liquor. Typically the flow rate of the non-reactive gas is between about 10 cc and about 2000 cc (measured at 760 mm Hg, −15° C) per hour per gram of indene recovered. Preferably, the flow rate is between about 100 and about 300 cc (measured at 760 mm Hg, −15° C) per hour per gram of indene recovered. It is critical that the temperature of the gas be between the freezing temperature and the co-crystallization temperature of the mixture. Gas above the freezing temperature will reduce the amount of indene recovered and gas below the co-crystallization temperature will lower the purity of the recovered product. Using the aforementioned conditions, flushing and vaporization of the residual mother liquor from the crystalline indene generally requires from about two to about eight hours.

Purities of 99 weight percent are achieved by the process of the present invention with a recovery of 60 to 70 weight percent of the original indene. Maximum recovery is accomplished by limiting the duration of the vaporization to the minimum acceptable purity because the gas flow does remove some of the crystalline indene present. For example, production of 95 weight percent pure indene from a mixture containing 90 percent indene can be accomplished with a total indene recovery of about 90 percent.

The following examples are given to illustrate the invention and should not be construed as limiting its scope. All percentages used in the following examples are by weight unless otherwise indicated.

APPARATUS AND GENERAL OPERATING PROCEDURE

In the following working examples, a two-piece apparatus having an upper and a lower unit is used. The lower unit includes a vertically oriented glass cylinder having a machined surface at its top and an abrupt taper to a stopcock at its bottom. A glass frit of about 1.5 in. in diameter with a pore size of about 0.1 mm, which serves as a filter is fitted in the cylinder just before the taper. The downstream side of the stopcock is connected to a vacuum means. The cylinder has a glass jacket with inlet and outlet fittings which are respectively connected to a supply and a return of a liquid refrigerant such as glycol. The lower unit serves to contain the mixture while it is being crystallized and while vaporization is being effected.

The upper unit is bell shaped, constructed of glass, and serves as a cap for the cylindrical lower unit. The upper unit has a machined surface and rubber gasket at its lower end and a fitting at its upper end to admit a gas and a seal for the agitator shaft. A motor is provided to turn the agitator shaft the paddles of which sweep substantially the volume of the lower unit. The upper unit supports an agitator shaft and forms an airtight seal with the lower unit.

A heat exchanger constructed of steel is provided to cool the gas to an operating temperature. The shell side is provided with fittings connected to a supply and a return of the liquid refrigerant. The tube side contains the gas and is provided with inlet and outlet fittings.

To prepare for a recovery, the stopcock is closed and the liquid mixture is poured into the lower unit. The upper unit with agitator is fitted into place and sealed. Agitation of the mixture is begun and the temperature of the mixture is lowered to the freezing temperature of the mixture but at least about 5° C above the co-crystallization temperature of the mixture. The temperature is lowered to between about −10° C to about −20° C over approximately a two-hour period. The agitator is then stopped. The stopcock is opened to a vaccum of about 25 in. Hg while a gas which has been cooled to a temperature in the range detailed above for the mixture is admitted through the upper unit. Air at a temperature of about −15° C is used. The opening of the stopcock allows the bulk of the mother liquor to pass from the lower unit through the frit. The residual mother liquor is vaporized by continuing to pass the cooled gas through the residual wet solid for about one hour. Typically, the gas passes through the wet solid at a rate of about 100 to 2000 cc per hour per g of compound recovered. At the end of the vaporization step, the vacuum is disconnected and a filter cake of dry solid substantially free of the mother liquor is collected.

The following examples are given to illustrate the invention and should not be construed as limiting its scope. All percentages used in the following examples are by weight unless otherwise indicated.

EXAMPLE 1

A mixture of 200 g of crude indene is poured into the lower unit. The mixture contains 92.2 percent indene as well as assorted other hydrocarbons such as isopropyl toluene, diethyl benzene, trimethyl benzene, methyl indene, indane, naphthalene, and biphenyl (the first six of which have melt points below that of indene and the last two of which have melt points above indene). This mixture is cooled with agitation to −13° C over a 2-hour period to form a wet solid composed substantially of crystalline indene. A filtrate of mother liquor is pulled through the stopcock by means of the vaccum. Vaporization of the remaining material with −13° C air for two hours removes a substantial part of the residual mother liquor to form a filter cake of dry solid. The air flow rate is about two liters per minute. The filtrate is weighed and found to contain 74.0 g. It is analyzed by gas chromatography and is found to be 84.16 percent indene. The filter cake weighs 112.0 g and upon analysis by gas chromatography is found to contain 99.78 percent indene. The total mass loss due to vaporization is 7 percent. The indene recovery is 60 percent of that present in the mixture.

This example illustrates that through practice of the invention about 60 percent of the indene present in a mixture is recovered in a purity of greater than 99 weight percent.

EXAMPLE 2

A 100.0 g portion of the crude indene mixture of Example 1 is poured into the lower unit. The mixture is cooled with agitation over a two-hour period to −20° C. A filtrate of mother liquor is pulled through the stopcock by means of the vacuum. Vaporization with −15° C air for two hours removes much of the remaining mother liquor and forms a dry solid filter cake. The air flow rate is about 2 liters per minute. Thirty-one grams of filtrate are recovered and by gas chromatography analysis the material is found to contain 81.54 percent indene. The filter cake weighs 64.0 g and upon analysis by gas chromatography is found to contain 99.21 percent indene. Five grams or 5 percent is lost in vaporization. Sixty-nine percent of the indene present in the mixture is recovered.

Again product purity in excess of 99 percent is obtained. The slightly colder operating temperature of −15° C results in a slightly lower purity but a higher recovery of total indene and a lower mass loss due to vaporization.

What is claimed is:

1. A process for the recovery of indene in ultrahigh purity from liquid hydrocarbon mixtures, the mixtures comprising indene and organic impurities of which at least one has a melt point above indene and of which at least one has a melt point below indene, the mixture having a co-crystallization temperature at least about 5° C lower than the freezing temperature of the mixture, the process comprising:
   (a) crystallizing a substantial portion of the indene from the mixture to form a slurry composed of mother liquor and crystals of indene; and
   (b) separating the impurities from the resulting crystals by passing a non-reactive gas at a temperature in the range between the freezing and the co-crystallization temperatures of the mixture over the surfaces of the crystals to remove said impurities while maintaining the crystals and the residual mother liquor at a temperature in the range between the freezing and the co-crystallization temperature of the mixture.

2. The process of claim 1 wherein the liquid mixture contains at least 85 weight percent indene and wherein the crystallization is brought about by lowering the temperature of the liquid mixture.

3. The process of claim 1 wherein the crystals are larger than about 0.2 mm in each of the three dimensions.

4. The process of claim 1 wherein (b) comprises mechanically separating a portion of the mother liquor from the slurry containing the crystals and then passing a non-reactive gas over the surfaces of the crystals and the residual mother liquor while maintaining the crystals and the residual mother liquor at a temperature in the range between the freezing and the co-crystallization temperatures of the mixture.

5. The process of claim 1 for the recovery of indene in a purity greater than 99 weight percent from liquid hydrocarbon mixtures wherein:

(a) the crystallizing occurs at a temperature of between about $-10°$ C and about $-20°$ C, (b) the crystals of indene are larger than about 2 mm in each of the three dimensions, and (c) the flow rate of the reactive gas is between about 100 and about 300 cc (measured at 760 mm Hg, $-15°$ C) per hour per gram of indene recovered.

6. The process of claim 5 wherein the temperature of the crystals of indene and the residual mother liquor is maintained between about $-10°$ C and about $-20°$ C while passing the non-reactive gas over the surfaces of the crystals.